(12) United States Patent
Lust et al.

(10) Patent No.: US 9,421,127 B2
(45) Date of Patent: Aug. 23, 2016

(54) PUNCTAL PLUGS

(71) Applicant: Johnson & Johnson Vision Care, Inc., Jacksonville, FL (US)

(72) Inventors: Victor Lust, Jacksonville, FL (US); Phillip King Parnell, Sr., Jacksonville, FL (US); Vincent G. McAteer, Orange Park, FL (US); Brian Schwam, Jacksonville, FL (US); Hassan Chaouk, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 661 days.

(21) Appl. No.: 13/682,825

(22) Filed: Nov. 21, 2012

(65) Prior Publication Data

US 2013/0131612 A1   May 23, 2013
US 2016/0206473 A9   Jul. 21, 2016

Related U.S. Application Data

(63) Continuation-in-part of application No. 12/749,085, filed on Mar. 29, 2010, now abandoned.

(60) Provisional application No. 61/165,417, filed on Mar. 31, 2009.

(51) Int. Cl.
*A61F 9/00* (2006.01)
*A61M 31/00* (2006.01)
*A61K 9/00* (2006.01)
*A61F 9/007* (2006.01)

(52) U.S. Cl.
CPC ......... *A61F 9/0026* (2013.01); *A61F 9/00772* (2013.01); *A61K 9/0051* (2013.01); *A61M 31/002* (2013.01); *A61F 9/0017* (2013.01)

(58) Field of Classification Search
USPC .................................. 604/294, 298
See application file for complete search history.

(56) References Cited

U.S. PATENT DOCUMENTS

| | | |
|---|---|---|
| 3,906,551 A | 9/1975 | Otter |
| 3,949,750 A | 4/1976 | Freeman |
| 4,478,544 A | 10/1984 | Strand |
| 4,582,265 A | 4/1986 | Petronelli |
| 4,607,865 A | 8/1986 | Hughes |
| 4,660,546 A | 4/1987 | Herrick |
| 4,754,812 A | 7/1988 | Gentry |
| 4,778,008 A | 10/1988 | Gonzalez |
| 4,900,066 A | 2/1990 | Brammer |
| 4,915,684 A | 4/1990 | MacKeen et al. |
| 4,959,048 A | 9/1990 | Seder et al. |
| 4,989,902 A | 2/1991 | Putch |
| 5,160,172 A | 11/1992 | Gariepy |

(Continued)

FOREIGN PATENT DOCUMENTS

| | | |
|---|---|---|
| JP | 2002/529144 | 9/2002 |
| JP | 2008/18234 | 1/2008 |

(Continued)

OTHER PUBLICATIONS

Notification of Reasons for Rejection for Application No. 2012-503554 dated Jan. 7, 2014.

*Primary Examiner* — Paula L. Craig (57) ABSTRACT

Punctal plugs for delivering therapeutic agents have a body, a portion into which the therapeutic agent is held, a winding about the body, and an enlarged portion or anchor at an end.

8 Claims, 3 Drawing Sheets

(56) References Cited

U.S. PATENT DOCUMENTS

| | | |
|---|---|---|
| 5,197,546 A | 3/1993 | Murray |
| 5,283,063 A * | 2/1994 | Freeman ............... 424/427 |
| 5,318,513 A * | 6/1994 | Leib et al. ............... 604/8 |
| 5,334,137 A | 8/1994 | Freeman |
| 5,375,670 A | 12/1994 | Ekwall |
| 5,404,944 A | 4/1995 | Lynde |
| 5,417,651 A * | 5/1995 | Guena et al. ............... 604/8 |
| 5,423,777 A | 6/1995 | Tajiri et al. |
| 5,723,005 A | 3/1998 | Herrick |
| 5,826,584 A | 10/1998 | Schmitt |
| 5,830,171 A * | 11/1998 | Wallace ............... 604/8 |
| 5,962,548 A | 10/1999 | Vanderlaan et al. |
| 5,993,407 A * | 11/1999 | Moazed ............... 604/8 |
| 6,016,806 A * | 1/2000 | Webb ............... 128/846 |
| 6,020,445 A | 2/2000 | Vanderlaan et al. |
| 6,027,470 A * | 2/2000 | Mendius ............... 604/8 |
| 6,041,785 A | 3/2000 | Webb |
| 6,082,362 A | 7/2000 | Webb |
| 6,099,852 A | 8/2000 | Jen |
| 6,149,684 A | 11/2000 | Herrick |
| 6,196,993 B1 | 3/2001 | Cohan |
| 6,234,175 B1 * | 5/2001 | Zhou et al. ............... 128/887 |
| 6,254,562 B1 | 7/2001 | Fouere |
| 6,290,684 B1 * | 9/2001 | Herrick ............... 604/294 |
| 6,367,929 B1 | 4/2002 | Maiden et al. |
| 6,629,533 B1 | 10/2003 | Webb et al. |
| 6,822,016 B2 | 11/2004 | McCabe et al. |
| 6,994,684 B2 | 2/2006 | Murray |
| 7,080,693 B2 | 7/2006 | Walker |
| 7,204,253 B2 | 4/2007 | Mendius et al. |
| 7,510,541 B2 * | 3/2009 | Hanna ............... 604/9 |
| D590,935 S | 4/2009 | Becker |
| 7,677,303 B2 | 3/2010 | Coronado |
| 7,736,326 B2 | 6/2010 | Fouere et al. |
| 7,785,285 B2 | 8/2010 | Kurihashi |
| 7,922,702 B2 | 4/2011 | Lazar |
| 8,109,339 B2 | 2/2012 | Xu |
| 8,333,726 B2 | 12/2012 | Rapacki |
| 8,439,865 B2 * | 5/2013 | Lust et al. ............... 604/93.01 |
| 9,259,351 B2 * | 2/2016 | Lust ............... A61F 9/0026 |
| 9,259,352 B2 * | 2/2016 | Lust ............... A61F 9/0026 |
| 2004/0254516 A1 * | 12/2004 | Murray et al. ............... 604/8 |
| 2005/0045188 A1 | 3/2005 | Mendius |
| 2005/0232972 A1 | 10/2005 | Odrich |
| 2006/0020248 A1 | 1/2006 | Prescott |
| 2006/0020253 A1 | 1/2006 | Prescott |
| 2006/0100700 A1 | 5/2006 | Bernard |
| 2006/0276738 A1 | 12/2006 | Becker |
| 2007/0243230 A1 | 10/2007 | De Juan et al. |
| 2007/0269487 A1 | 11/2007 | De Juan et al. |
| 2007/0298075 A1 | 12/2007 | Borgia et al. |
| 2007/0299515 A1 * | 12/2007 | Herrick, II ............... 623/4.1 |
| 2007/0299516 A1 | 12/2007 | Cui et al. |
| 2008/0030025 A1 | 2/2008 | Vogel |
| 2008/0038317 A1 | 2/2008 | Chang |
| 2008/0045911 A1 | 2/2008 | Borgia et al. |
| 2008/0181930 A1 | 7/2008 | Rodstrom |
| 2009/0036982 A1 | 2/2009 | Aharoni et al. |
| 2009/0104243 A1 | 4/2009 | Utkhede et al. |
| 2009/0104248 A1 | 4/2009 | Rapacki |
| 2009/0306608 A1 | 12/2009 | Li et al. |
| 2010/0114309 A1 | 5/2010 | De Juan et al. |
| 2010/0137818 A1 | 6/2010 | Odrich |
| 2010/0163250 A1 | 7/2010 | Schultz |
| 2010/0209477 A1 | 8/2010 | Butuner et al. |
| 2010/0256557 A1 * | 10/2010 | Lust et al. ............... 604/93.01 |
| 2010/0256578 A1 * | 10/2010 | Lust et al. ............... 604/294 |
| 2012/0049513 A1 | 3/2012 | Herrera |
| 2012/0116504 A1 | 5/2012 | Lyons et al. |
| 2013/0090611 A1 * | 4/2013 | Lust et al. ............... 604/294 |
| 2013/0123718 A1 * | 5/2013 | Lust et al. ............... 604/294 |
| 2013/0131612 A1 | 5/2013 | Lust |

FOREIGN PATENT DOCUMENTS

| | | |
|---|---|---|
| TW | 200808372 A | 2/2008 |
| WO | WO 2007/149771 A2 | 12/2007 |
| WO | WO 2008/083118 A1 | 7/2008 |
| WO | WO2008094989 A2 | 8/2008 |
| WO | WO2008094989 A3 | 4/2009 |

\* cited by examiner

PUNCTAL PLUGS

CROSS REFERENCE TO RELATED APPLICATIONS

This patent application is a continuation-in-part of U.S. patent application Ser. No. 12/749,085, filed Mar. 29, 2010, which claims the benefit of U.S. Provisional Patent Application No. 61/165,417, filed Mar. 31, 2009.

BACKGROUND OF THE INVENTION

1. Field of the Invention

The present invention relates to devices for delivering therapeutic agents to one or more of the eye, nose and throat, and more particularly, to punctal plugs for delivering therapeutic agents to one or more of the eye, nose and throat.

2. Discussion of the Related Art

Human tears are secreted by the lacrimal gland and flow across the surface of the eye to a shallow pool, known as the lacrimal lake, located where the eyelids come together at their inner ends. From there, the tears drain through small openings in each of the upper and lower eyelids, termed the superior lacrimal punctum and the inferior lacrimal punctum, respectively. From the superior and inferior puncta, the tears pass into each of the superior and inferior lacrimal canaliculus, respectively, which are duct-like pathways that lead to the lacrimal sac. The lacrimal sac is the superior, expanded portion of the nasolacrimal duct, which drains tears into the nasal system. Active and/or therapeutic agents can thus be delivered to the nose and throat through the lacrimal canaliculi, which lead into the nasolacrimal duct.

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea, conjunctiva or sclera and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects, while injections pose the risk of infection, discomfort, bleeding or perforation of the globe.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

It is known to use devices that may be inserted into one or more of an orifice of an individual's eye, such as a lacrimal punctum, to deliver active agents. These punctal plugs may be configured for customized delivery of the active agents in terms of dosage and duration; however, as each individual's eye anatomy is unique, placement and anchoring of the punctal plug in the puncta may present certain difficulties. Accordingly, there exists a need for punctal plugs that are configured for ease of placement and anchoring while delivering an active agent over a predetermined treatment period.

SUMMARY OF THE INVENTION

The punctal plugs in accordance with the present invention overcome the limitations associated with the prior art as briefly described above.

In accordance with one aspect, the present invention is directed to a lacrimal insert for delivering one or more active agents. The lacrimal insert for delivering one or more active agents comprises an elongated main body having a first end and a second end, the elongated main body including a reservoir, a collarette connected to the first end of the main body and having at least one opening in fluid communication with the reservoir, the collarette being concentrically positioned relative to the elongated main body, and a head section connected to the second end of the elongated main body, the head section including a flange portion having a substantially disc shaped configuration, and a cone portion, the flange portion and the cone portion being non-concentrically positioned relative to the elongated main body.

In accordance with another aspect, the present invention is directed to a lacrimal insert for delivering one or more active agents. The lacrimal insert for delivering one or more active agents comprises an elongated main body having a first end and a second end, the elongated main body including a reservoir, a collarette connected to the first end of the main body and having at least one opening in fluid communication with the reservoir, the collarette being concentrically positioned relative to the elongated main body, and a head section connected to the second end of the elongated main body, the head section including a flange portion having a lower surface with a spherical cone shape and an upper surface that is substantially bowl shaped, and a cone portion, the flange portion and the cone portion being non-concentrically positioned relative to the elongated main body.

In accordance with still another aspect, the present invention is directed to a lacrimal insert for delivering one or more active agents. The lacrimal insert for delivering one or more active agents comprises an elongated main body having a first end and a second end, the elongated main body including a reservoir and a threaded portion, a collarette connected to the first end of the main body and having at least one opening in fluid communication with the reservoir, the collarette being concentrically positioned relative to the elongated main body, and a head section connected to the second end of the elongated main body, the head section including a flange portion having a lower surface with a spherical cone shape and an upper surface that is substantially flat, and a cone portion, the flange portion and the cone portion being non-concentrically positioned relative to the elongated main body.

The present invention is directed to punctual plugs sized to pass through a lacrimal punctum and be positioned within a lacrimal canaliculis of the eyelid and which comprises one or more therapeutic agents for controlled release into the eye. The punctual plug is configured for easy insertion and long term stability. The plug is configured to hold the one or more therapeutic agents and release these one or more agents into the eye for treatment of a particular condition of the eye.

The exemplary punctal plugs of the present invention are designed to improve anchoring in the anatomy. The devices utilize various configurations, including offset distal ends and threads to improve anchoring and retention. These design modifications have minimal impact on manufacturability and cost.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Punctal plugs have been in use for decades now to treat conditions of dry eye. More recently they have gained attention for use as drug delivery systems for the treatment of ocular diseases and conditions. Several challenges exist with formulating a drug to release at the desired daily rate and or dose that will give efficacy while limiting adverse events.

Diffusion based drug delivery systems are characterized by the release rate of a drug. This is dependent on its diffusion through an inert water insoluble membrane barrier. There are basically two diffusion designs: reservoir devices and matrix devices. Reservoir devices are those in which a core of drug is surrounded by a polymeric membrane. The nature of the membrane determines the rate of release of a drug from system. The process of diffusion is generally described by a series of equations governed by Fick's first law of diffusion. A matrix device consists of drug dispersed homogenously throughout a polymer structure.

Reservoir and matrix drug delivery systems are considered diffusion based sustained release systems and constitute any dosage form that provides medication over an extended period of time. The goal of a sustained release system is to maintain therapeutic levels of drug for an extended period and this is usually accomplished by attempting to obtain zero-order release from the sustained release system. Sustained release systems generally do not attain this type of release profile but try to approximate it by releasing the drug in a slow first order manner. Over an extended period of time, the drug release rate from reservoir and matrix sustained release systems will decay and become non therapeutic.

Zero-order drug release constitutes drug release from a drug delivery system at a steady sustained drug release rate, that is, the amount of drug that is released from the drug delivery system over equal time intervals does not decay and remains at the therapeutic level. This "steady sustained release drug delivery system" is referred to as a zero-order drug delivery system and has the potential to provide actual therapeutic control by its controlled release. Another drug release profile is referred to as pulsatile drug delivery. Pulsatile drug delivery is intended to release a therapeutic amount of a therapeutic agent at regular intervals.

The punctal plugs in accordance with the present invention may be utilized to deliver active and/or therapeutic agents to one or both of the nasolacrimal duct and to the tear film of the eye. In one exemplary embodiment, the punctal plug comprises a main body, including reservoir, and having a proximal end and a distal end, a collarette connected to the proximal end of the main body, and a head section, including a flange structure that is substantially flat on both sides, and a substantially cone shaped section, aligned with the distal end of the main body. The collarette is concentrically aligned with the main body while the head section is non-concentrically aligned with the main body. In another exemplary embodiment, the punctal plug comprises a main body, including a reservoir, and having a proximal end and a distal end, a collarette connected to the proximal end of the main body, and a head section, including a flange structure that is substantially flat on one side and rounded on the other side, and a substantially cone shaped section, connected to the distal end of the main body. The collarette is concentrically aligned with the main body while the head section is non-concentrically aligned with the main body. The cone shaped section of this exemplary embodiment is more rounded that the previously described exemplary embodiment. In yet another exemplary embodiment, the punctal plug comprises a main body, including a reservoir, and having a proximal end and a distal end, a collarette connected to the proximal end of the main body, and a head section, including a flange structure that is substantially flat on one side and rounded on the other side, and a substantially cone shape section, connected to the distal end of the main body. The collarette is concentrically aligned with the main body while the head section is non-concentrically aligned with the main body. The cone shaped section of this exemplary embodiment is the same as the previously described exemplary embodiment. The main body; however, differs from the other exemplary embodiments in that it also comprises threads from its proximal end to its distal end. A detailed description of each of the exemplary embodiments, is set forth below.

The present invention encompasses punctal plugs for the delivery of active agents to one or both of the tear film of the eye and to the nasolacrimal duct. The punctal plugs preferably are inserted into the inferior lacrimal canaliculis, the superior lacrimal canaliculus, or both the inferior and superior lacrimal canaliculus. If the punctal plugs are being used to deliver active agents to the tear fluid of the eye, the punctal plugs preferably have a collarette at one end of the main body as described above. The collarette is a portion of the punctal plug that extends radially, outward from the end of the body to a degree sufficient and having a size and a shape such that at least a portion of the collarette will extend beyond and be exterior to the lacrimal punctum after insertion of the punctal plug into the lacrimal canaliculus. Typically, the collarette will extend about 0.2 to about 1 mm beyond the main body. Essentially, the collarette rests against the interior of the lacrimal punctum and keeps the punctal plug from slipping down into the lacrimal canaliculus so that contact between the punctal plug and the tear film of the eye is maintained. If the punctal plugs are being utilized to deliver active agent to the nasolacrimal duct, the punctal plugs may not comprise a collarette so that they may be inserted to a sufficient depth within one or both of the lacrimal canaliculi such that the active agent is released into the lacrimal sac.

As used herein, the term "punctal plug" refers to a device of a size and shape suitable for insertion into the inferior or superior lacrimal canaliculus of the eye through, respectively, the inferior or superior lacrimal punctum.

As used herein, the term "active agent" refers to an agent capable of treating, inhibiting, or preventing a disorder or a disease. Exemplary active agents include pharmaceuticals and nutraceuticals. Preferred active agents are capable of treating, inhibiting, or preventing a disorder or a disease of one or more of the eye, nose and throat.

As used herein, the term "a material that is at least partially water-soluble" refers to a material that exhibits a level of solubility in water sufficient to result in detectable dissolution of the material upon exposure to an aqueous environment.

As used herein, the term "a material that is biodegradable" refers to a material that degrades to a detectable degree upon exposure to biologically active substances typically present in mammals.

As used herein, the term "a material that is insoluble in water" refers to a material that does not dissolve to a substantial degree upon exposure to water.

As used herein, the phrase "a material that is non-biodegradable" refers to a material that does not degrade to a substantial degree upon exposure to biologically active substances typically present in mammals.

As used herein, the phrase "body that is impermeable to active agent" refers to a body through which only an insubstantial amount of active agent may pass.

As used herein, the term "polymeric material" refers to a material made of one or more types of polymers that is capable of containing at least one active agent and releasing the active agent, for example, when the polymers dissolve or degrade, when the active agent diffuses from the polymers, or when a pro-drug is used in which the active agent is attached to the polymers and then released by being cleaved from the material.

As used herein, the term "opening" refers to an opening in the body of a punctal plug of a size and shape through which the active agent can pass. Preferably, only the active agent can pass through the opening. The opening, for example, may be a hole covered with a membrane, mesh, grid or it may be uncovered. The membrane, mesh, or grid may be one or more of porous, semi-porous, permeable, semi-permeable, and biodegradable.

As used herein, the phrase "flexible material" refers to a material that is not rigid and that substantially conforms to the surface of whatever object the material contacts.

As used herein, the phrase "the reservoir and the body are coterminous" indicates that the reservoir is substantially all of the body. A collarette can be attached to the body when the reservoir and body are coterminous, but the collarette would not be considered to be part of the body.

As used herein, the phrase "refilled with active agent" refers to adding any detectable amount of active agent to the reservoir of a punctal plug.

Figure 1A:
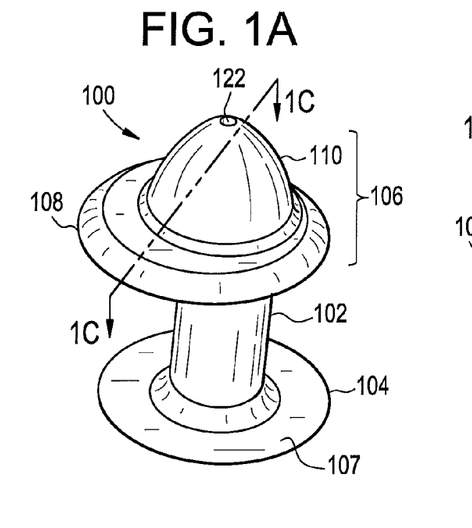
FIGS. 1A and 1B are diagrammatic views of a first exemplary punctal plug in accordance with the present invention.
Figure 1B:
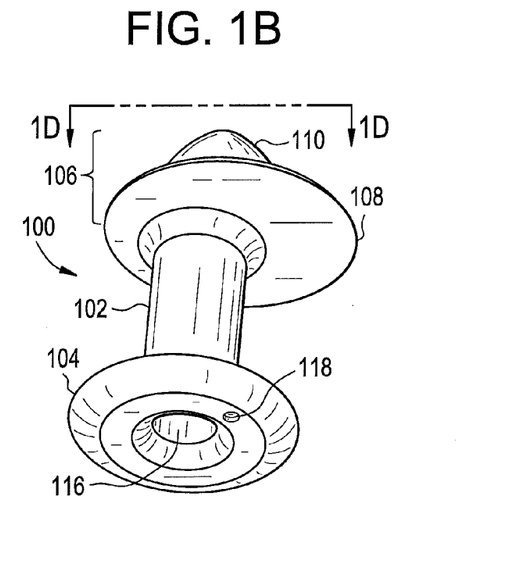
Figure 1C:
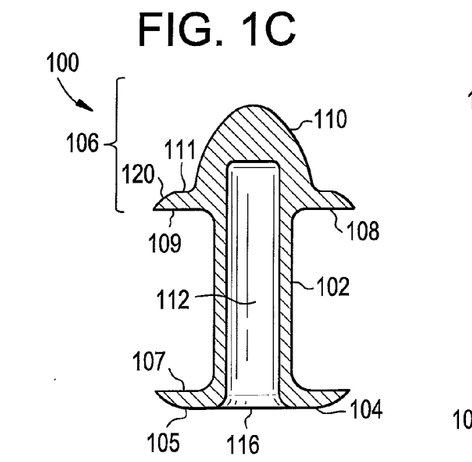
FIGS. 1C and 1D are sectional views of the first exemplary punctal plugs illustrated in FIGS. 1A and 1B taken along section lines 1C-1C and 1D-1D.
Figure 1D:
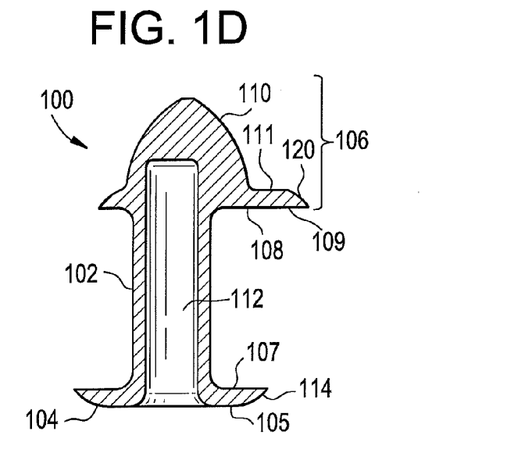

Referring now to FIGS. 1A-1D, there is illustrated, in multiple views, a first exemplary embodiment of a punctal plug 100. The punctal plug 100 comprises a main body 102, a collarette 104 and a head section 106, including a flange portion 108 and a cone section 110. The main body 102 includes a reservoir 112 which extends from the collarette 104 into the head section 106. The main body 102 comprises a substantially cylindrical shape as does the reservoir 112 therein. It is important to note that the main body 102 may comprise any suitable shape and/or size. The reservoir 112 may also comprise any suitable shape, size and material to hold and controllably release the active agent. Therefore, the reservoir 112 may extend to any portion of the device including the head section 106.

The collarette 104 comprises a substantially disc shaped structure with a substantially flat upper surface 105, a substantially flat lower surface 107 and a beveled edge 114, and is concentrically aligned with the main body 102. In other words, the central axis of the collarette 104 is aligned with the central axis of the main body portion 102. The collarette 104 is a section of the punctal plug 100 that extends radially from the main body portion 102 to a degree sufficient, and having a size and shape, such that at least a portion of the collarette 104 will extend beyond and be exterior to the lacrimal punctum after inserting of the punctal plug 100 into the lacrimal canaliculus. The collarette 104 also comprises an opening 116 which is in fluid communication with the reservoir 112. Although a single opening 116 is illustrated, multiple openings may be utilized. The opening 116 allows fluid in the reservoir 112 to exit the punctal plug 100 and enter the eye via the tear film. In this exemplary embodiment, the active agent simply diffuses out of the reservoir 112. The rate at which the active agent diffuses from the reservoir 112 depends on a number of factors, including the active agent itself and the materials mixed with the active agent as is discussed in greater detail subsequently. In alternate exemplary embodiments, active devices such as pumps may be utilized to deliver the active agents. The collarette 104 also comprises a mark 118 for proper positioning of the punctal plug 100. As will be described in greater detail subsequently, the punctal plug 100 has to be positioned such that it anchors in the anatomy to achieve the best fit possible; accordingly, the mark 118 indicates the direction of greater offset of the head section 106 relative to the main body 102. The mark 118 may comprise any suitable indicia which is visible to the physician placing the punctal plug 100. For example, the mark 118 may simply comprise a hole or dimple on the upper surface 105 of the collarette 104.

The head section 106 is non-concentrically aligned with the main body 102. In other words, the central axis of the flange portion 108 and the central axis of the cone section 110 are not aligned with the central axis of the main body 102. This offset or non-concentric placement allows for better anchoring of the punctal plug in the canaliculus. Based upon eye anatomy, it should be understood that this offset design allows for better anchoring regardless of specific anatomical variations. Although the insertion force for the punctal plug 100 may be greater, the removal force will also be greater. Essentially, the head section 106 is an enlarged portion of the punctal plug 100 that is of suitable size and shape for securing the punctal plug 100 in the lacrimal canaliculus. The flange portion 108 comprises a substantially disc shaped structure with a substantially flat upper surface 109, a substantially flat lower surface 111, and a beveled edge 120. The cone section 110 comprises a rounded dome structure. The cone section 110 may comprise any suitable shape, including an oblique circular cone, a right elliptical cone or an oblique elliptical cone; however, the cone section 110 preferably comprises a right circular cone. The cone section 110 and the flange portion 108 may be connected by any suitable means, including adhesives, overmoulding and welding; however, in a preferred exemplary embodiment, they are formed as a single, unitary structure. In certain exemplary embodiments, the cone section 110 may comprise an opening 122 through which the active agent may be delivered into the nasolacrimal duct. This opening may be in addition to the opening 116 in the collarette 104 or as an alternate thereto. The opening 122 is in fluid communication with the reservoir 112. Either opening 116 or 122 may be utilized to refill the reservoir 112. Essentially, the opening through which the active agent is released from the punctal plug 100 may be located at either end thereof, or from any lateral surface thereof.

The punctal plug 100 may be fabricated from any number of suitable biocompatible materials and manufactured utilizing any suitable techniques as set forth in greater detail subsequently. The reservoir 112 may be filled with one or more active agents to treat a wide variety of conditions as set forth below.

Figure 2A:
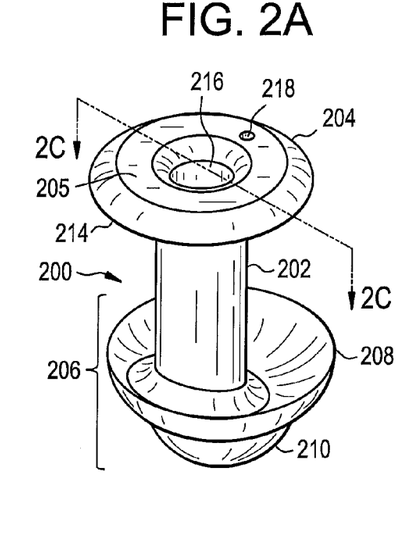
FIGS. 2A and 2B are diagrammatic views of a second exemplary punctal plug in accordance with the present invention.
Figure 2B:
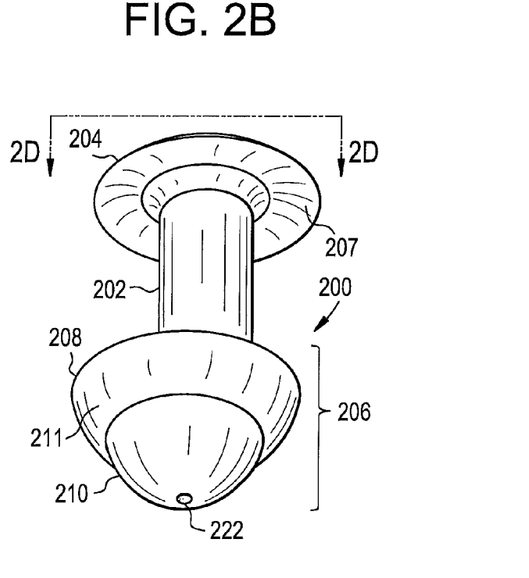
Figure 2C:
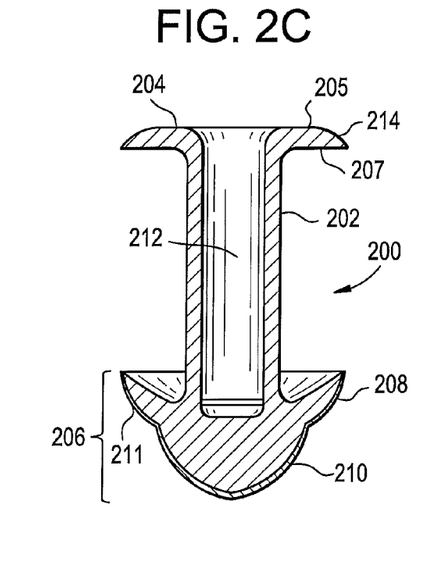
FIGS. 2C and 2D are sectional views of the second exemplary punctal plugs illustrated in FIGS. 2A and 2B taken along section lines 2C-2C and 2D-2D.
Figure 2D:
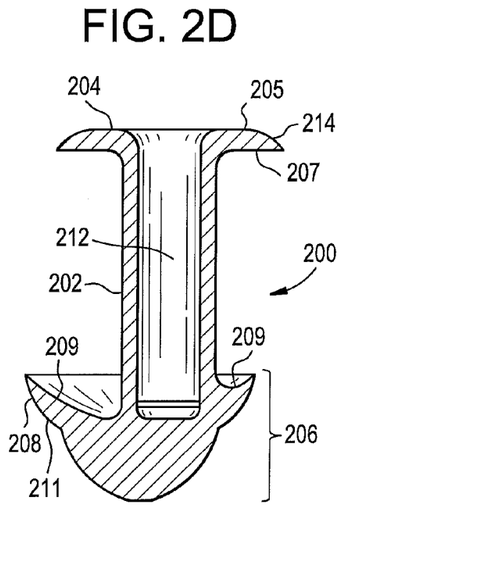

Referring now to FIGS. 2A-2D, there is illustrated, in multiple views, a second exemplary embodiment of a punctal plug 200. The punctal plug 200 comprises a main body 202, a collarette 204 and a head section 206, including a flange portion 208 and a cone section 210. The main body 202 includes a reservoir 212 which extends from the collarette 204 into the head section 206. The main body 202 comprises a substantially cylindrical shape as does the reservoir 212 therein. It is important to note that the main body 202 may comprise any suitable shape and/or size. The reservoir 212 may also comprise any suitable shape, size and material to hold and controllably release the active agent. Therefore, the reservoir 212 may extend to any portion of the device including the head section 206.

The collarette 204 comprises a substantially disc shaped structure with a substantially flat upper surface 205, a substantially flat lower surface 207 and a beveled edge 214, and is concentrically aligned with the main body 202. In other words, the central axis of the collarette 204 is aligned with the central axis of the main body portion 202. The collarette 204 is a section of the punctal plug 200 that extends radially from the main body portion 202 to a degree sufficient, and having a size and shape, such that at least a portion of the collarette 204 will extend beyond and be exterior to the lacrimal punctum after inserting of the punctal plug 200 into the lacrimal canaliculus. The collarette 204 also comprises an opening 216 which is in fluid communication with the reservoir 212. Although a single opening 216 is illustrated, multiple openings may be utilized. The opening 216 allows fluid in the reservoir 212 to exit the punctal plug 200 and enter the eye via the tear film. In this exemplary embodiment, the active agent simply diffuses out of the reservoir 212. The rate at which the active agent diffuses from the reservoir 212 depends on a number of factors, including the active agent itself and the materials mixed with the active agent as is discussed in greater detail subsequently. In alternate exemplary embodiments, active devices such as pumps may be utilized to deliver the active agents. The collarette 204 also comprises a mark 218 for proper positioning of the punctal plug 200. As will be described in greater detail subsequently, the punctal plug 200 has to be positioned such that it anchors in the anatomy to achieve the best fit possible; accordingly, the mark 218 indicates the direction of greater offset of the head section 206. The mark 218 may comprise any suitable indicia which is visible to the physician placing the punctal plug 200. For example, the mark 218 may simply comprise a hole or dimple on the upper surface 205 of the collarette 204.

The head section 206 is non-concentrically aligned with the main body 202. In other words, the central axis of the flange portion 208 and the central axis of the cone section 210 are not aligned with the central axis of the main body 202. This offset or non-concentric placement allows for better anchoring of the punctal plug in the canaliculus. Based upon eye anatomy, it should be understood that this offset design allows for better anchoring regardless of specific anatomical variations. Although the insertion force for the punctal plug 200 may be greater, the removal force will also be greater. Essentially, the head section 206 is an enlarged portion of the punctal plug 100 that is of suitable size and shape for securing the punctal plug 200 in the lacrimal canaliculus. The flange portion 208 does not comprise a substantially disc shaped structure as in the first exemplary embodiment, but rather a unique rounded structure. As illustrated, the lower surface 211 of the flange 208 comprises a spherical cone shape with a different angle than the cone section 210 and an upper surface 209 that is substantially bowl shaped. Given its off axis attachment, the upper surface 209 also comprises two different depths. In the region which extends the farther from the main body 202, the upper surface 209 extends deeper towards the cone section 210 than the upper surface 209 closer to the main body 202. The upper rim of the flange portion 208 is at the same height, but the unique configuration and off axis or non-concentric positioning, allows for more secure anchoring in the canaliculus. The cone section 210 comprises a rounded dome structure. The cone section 210 may comprise any suitable shape, including an oblique circular cone, a right elliptical cone or an oblique elliptical cone; however, the cone section 210 preferably comprises a right circular cone. The cone section 210 and the flange portion 208 may be connected by any suitable means, including adhesives, overmoulding and welding; however, in a preferred exemplary embodiment, they are formed as a single, unitary structure. In certain exemplary embodiments, the cone section 210 may comprise an opening 222 through which the active agent may be delivered into the nasolacrimal duct. This opening may be in addition to the opening 216 in the collarette 204 or as an alternate thereto. The opening 222 is in fluid communication with the reservoir 212. Either opening 222 may be utilized to refill the reservoir 212. Essentially, the opening through which the active agent is released from the punctal plug 200 may be located at either end thereof, or from any lateral surface thereof. The rounded dome of this exemplary embodiment is more rounded than that of the rounded dome of the first exemplary embodiment illustrated in FIG. 1.

The punctal plug 200 may be fabricated from any number of suitable biocompatible materials and manufactured utilizing any suitable techniques as set forth in greater detail subsequently. The reservoir 212 may be filled with one or more active agents to treat a wide variety of conditions as set forth below.

Figures 3A, 3B:
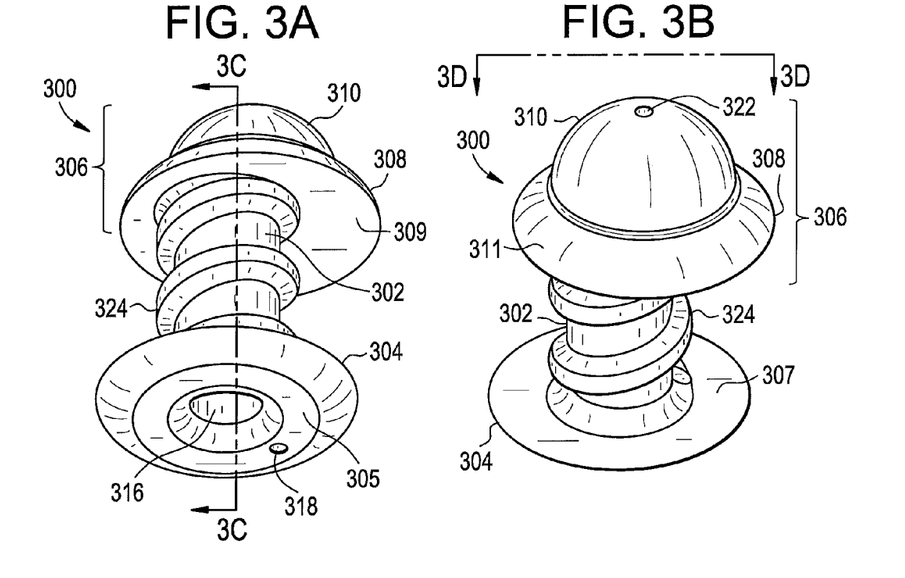
FIGS. 3A and 3B are diagrammatic views of a third exemplary punctal plug in accordance with the present invention.
Figure 3C:
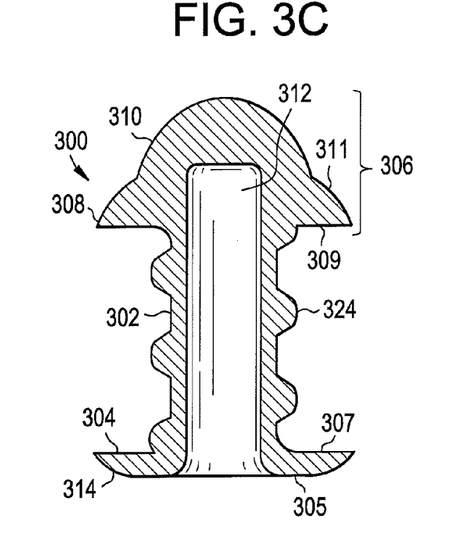
FIGS. 3C and 3D are sectional views of the third exemplary punctal plugs illustrated in FIGS. 3A and 3B taken along section lines 3C-3C and 3D-3D.
Figure 3D:
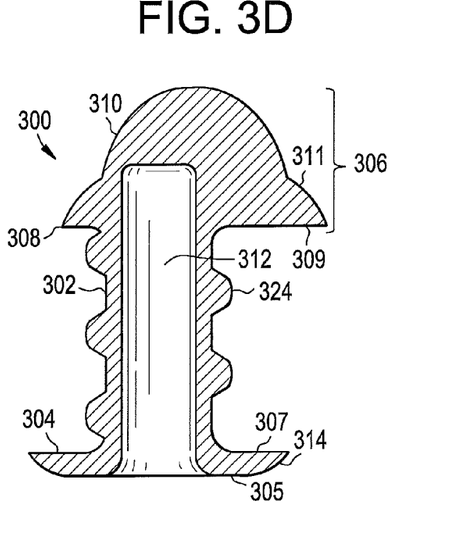

Referring now to FIGS. 3A-3D, there is illustrated, in multiple views, a third exemplary embodiment of a punctal plug 300. The punctal plug 300 comprises a main body 302, a collarette 304 and a head section 306, including a flange portion 308 and a cone section 310. The main body 302 includes a reservoir 312 which extends from the collarette 304 into the head section 306. The main body 302 comprises a substantially cylindrical shape as does the reservoir 312 therein. It is important to note that the main body 300 may comprise any suitable shape and/or size. The main body 302 also comprises a threaded portion or threads 324 running along the outer surface thereof. In the illustrated exemplary embodiment, the threads 324 extend from the collarette 304 to the head section 306. However, in alternate exemplary embodiments, the threads 324 may extend any suitable length along the body. The threads 324 may be formed directly on the surface of the main body 302 as part of a single, unitary monolithic structure, or the threads 324 may be separately formed from a suitable biocompatible material and attached to the main body 302 by any suitable means, such as gluing or welding. The threads 324 may comprise any suitable pitch and/or lead and preferably have rounded edges to prevent damage to the surrounding tissue. Essentially, a thread or screw thread is a helical structure for converting between rotational and linear movement, and is typically used as a fastener. In this exemplary embodiment, the threads 324 act as a fastener or anchor to secure the punctal plug 300 in position. The reservoir 312 may comprise any suitable shape, size and material to hold and controllably release the active agent. Therefore, the reservoir 312 may extend to any portion of the device including the head section 306.

The collarette 304 comprises a substantially disc shaped structure with a substantially flat upper surface 305, a substantially flat lower surface 307 and a beveled edge 314, and is concentrically aligned with the main body 302. In other words, the central axis of the collarette 304 is aligned with the central axis of the main body portion 302. The collarette 304 is a section of the punctal plug 300 that extends radially from the main body portion 302 to a degree sufficient, and having a size and shape, such that at least a portion of the collarette 304 will extend beyond and be exterior to the lacrimal punctum after inserting of the punctal plug 300 into the lacrimal canaliculus. The collarette 304 also comprises an opening 316 which is in fluid communication with the reservoir 312. Although a single opening 316 is illustrated, multiple openings may be utilized. The opening 316 allows fluid in the reservoir 312 to exit the punctal plug 300 and enter the eye via the tear film. In this exemplary embodiment, the active agent simply diffuses out of the reservoir 312. The rate at which the active agent diffuses from the reservoir 312 depends on a number of factors, including the active agent itself and the materials mixed with the active agent as is discussed in greater detail subsequently. In alternate exemplary embodiments, active devices such as pumps may be utilized to deliver the active agents. The collarette 304 also comprises a mark 318 for proper positioning of the punctal plug 300. As will be described in greater detail subsequently, the punctal plug 300 has to be positioned such that it anchors in the anatomy to achieve the best fit possible; accordingly, the mark 318 indicates the direction of greater offset of the head section 306 relative to the main body. The mark 318 may comprise any suitable indicia which is visible to the physician placing the punctal plug 300. For example, the mark 318 may simply comprise a hole or dimple on the upper surface 305 of the collarette 304.

The head section 306 is non-concentrically aligned with the main body 302. In other words, the central axis of the flange portion 308 and the central axis of the cone section 310 are not aligned with the central axis of the main body 302. This offset or non-concentric placement allows for better anchoring of the punctal plug in the canaliculus. Based upon eye anatomy, it should be understood that this offset design allows for better anchoring regardless of specific anatomical variations. Although the insertion force for the punctal plug 300 may be greater, the removal force will also be greater. Essentially, the head section 306 is an enlarged portion of the punctal plug 300 that is of suitable size and shape for securing the punctal plug 300 in the lacrimal canaliculus. The flange portion 308 does not comprise a substantially disc shaped structure as in the first exemplary embodiment, but rather a unique rounded structure. As illustrated, the lower surface 311 of the flange 308 comprises a spherical cone shape with a different angle than the cone section 310 and an upper surface 309 that is substantially flat, similar to the first exemplary embodiment. The upper rim of the flange portion 308 is at the same height, but the unique configuration and off axis or non-concentric positioning, allows for more secure anchoring in the canaliculus. The cone section 310 comprises a rounded dome structure. The cone section 310 may comprise any suitable shape, including an oblique circular cone, a right elliptical cone or an oblique elliptical cone; however, the cone section 310 preferably comprises a right circular cone. The cone section 310 and the flange portion 308 may be connected by any suitable means, including adhesives, overmoulding and welding; however, in a preferred exemplary embodiment, they are formed as a single, unitary structure. In certain exemplary embodiments, the cone section 310 may comprise an opening 322 through which the active agent may be delivered into the nasolacrimal duct. This opening may be in addition to the opening 316 in the collarette 304 or as an alternate thereto. The opening 322 is in fluid communication with the reservoir 312. Either opening 316 or 322 may be utilized to refill the reservoir 312. Essentially, the opening through which the active agent is released from the punctal plug 300 may be located at either end thereof, or from any lateral surface thereof. The rounded dome of this exemplary embodiment is more rounded than that of the rounded dome of the first exemplary embodiment illustrated in FIG. 1.

The punctal plug 300 may be fabricated from any number of suitable biocompatible materials and manufactured utilizing any suitable techniques as set forth in greater detail subsequently. The reservoir 312 may be filled with one or more active agents to treat a wide variety of conditions as set forth below.

In all three exemplary embodiments set forth above, the reservoir is configured to contain one or more active agents to be released by diffusion or any other suitable means. Therefore, the reservoir is preferably configured to hold a sufficient quantity of the one or more agents for a given period of time. The reservoir may also be configured for refilling through any of the openings therein for extended use. In each of the exemplary embodiments, the punctal plug is configured for secure anchoring and retention.

The main body of the punctal plug may be wholly or partially transparent or opaque. Optionally, the main body may include a tint or pigment that makes the plug easier to see when it is placed in a punctum.

The main body of the punctal plugs may be made of any suitable biocompatible material, including silicone, silicone blends, silicone co-polymers, for example, hydrophilic monomers of polyhydroxyethlymethacrylate ("pHEMA"), polyethylene glycol, polyvinylpyrrolidone, and glycerol, and silicone hydrogel polymers, for example, those described in U.S. Pat. Nos. 5,962,548, 6,020,445, 6,099,852, 6,367,929, and 6,822,016, incorporated herein in their entireties by reference. Other suitable biocompatible materials include polyurethane; polymethylmethacrylate; poly (ethylene glycol); poly(ethylene oxide); polypropylene glycol); poly(vinyl alcohol); poly(hydroxyethyl methacrylate); poly(vinylpyrrolidone) ("PVP"); polyacrylic acid; poly(ethyloxazoline); poly(dimethyl acrylamide); phospholipids, for example, phosphoryl choline derivatives; polysulfobetains; acrylic esters, polysaccharides and carbohydrates, for example, hyaluronic acid, dextran, hydroxyethyl cellulose, hydroxyl propyl cellulose, gellan gum, guar gum, heparan sulfate, chondritin sulfate, heparin, and alginate; proteins, for example, gelatin, collagen, albumin, and ovalbumin; polyamino acids; fluorinated polymers, for example, polytetrafluoroethylene ("PTFE"), polyvinylidene fluoride ("PVDF"), and teflon; polypropylene; polyethylene; nylon; poly/ethylvinyl acetate ("EVA"); poly/caprolactone; and poly/ethylene vinyl alcohol ("EVOH").

The surface of the punctal plug main body may be wholly or partially coated. The coating may provide one or more of lubriciousness to aid insertion, muco-adhesiveness to improve tissue compatibility, and texture to aid in anchoring the plug within the punctum. Examples of suitable coatings include gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like and combinations thereof.

Certain exemplary embodiments of the punctal plugs of the present invention have a main body made of a flexible material that conforms to the shape of whatever it contacts. Optionally, the punctal plug may have a collarette formed of either a less flexible material than that of the main body or material that too conforms to the shape of whatever it contacts. When a punctal plug having both a flexible main body and a less flexible collarette is inserted into the lacrimal canaliculus, the collarette rests on the exterior of the lacrimal punctum and the main body of the punctal plug conforms to the shape of the lacrimal canaliculus. The reservoir and the main body of such punctal plugs are preferably coterminous. That is, the reservoir of such punctal plugs preferably make up the entirety of the main body, except for the collarette.

In exemplary embodiments in which one or both of a flexible main body and collarette are used, the flexible main body and flexible collarette can be made of materials that include nylon, polyethylene terephthalate ("PET"), polybutylene terephthalate ("PBT"), polyethylene, polyurethane, silicone, silicone made from multiple precursors assisted by crosslinkers and catalysts, PTFE, PVDF, and polyolefins. Punctal plugs made of nylon, PET, PBT, polyethylene, PVDF, or polyolefins are typically manufactured utilizing extrusion, injection molding, or thermoforming. Punctal plugs made of latex, polyurethane, silicone, or PTFE are typically manufactured using solution casting processes.

The punctal plugs of the present invention comprise a reservoir within the main body, and the reservoir comprises an active agent-containing material. The material may be any material that is compatible with the active agent or agents to be delivered by the plug and is capable of releasing the active agent in the desired manner, for example, by dissolving or degrading of the material or diffusion of the active agent from the material. Any number of material may be used as the active agent-containing material including polymeric materials, both naturally occurring and synthetic, non-polymeric materials including glasses and clays, organic materials, inorganic materials including, porous ceramics, lipids, waxes and the like and combinations thereof. Preferably, the active agent containing-material is a polymeric material, in which at least one active agent is disposed on, dispersed throughout, or otherwise contained. The main body is preferably impermeable to the active agent, and the reservoir has at least one opening through which the active agent is released.

The main body has one or more openings communicating with the reservoir at a first end, a second end, or at another location on the main body. In particular exemplary embodiments of the invention, when such punctal plugs are inserted into the lacrimal canaliculus and have opening at the end of the body facing the eye, the active agent is released into the tear fluid of the eye. Alternately, if the punctal plug has an opening in the end of the main body facing the nasolacrimal duct, the active agent is released into the nasolacrimal duct. In those exemplary embodiments in which the punctal plug has opening at the end of the body facing the eye and another opening at the end of the body facing the nasolacrimal duct, the active agent is released into both the tear fluid of the eye and the nasolacrimal duct. For those punctal plugs with a collarette, the opening of such punctal plugs is preferably located within the collarette, preferably the central portion of the collarette. When such punctal plugs are inserted into the lacrimal canaliculus, the opening faces the eye, and the active agent is released into the tear fluid of the eye. The size of the opening will be from about 0.05 mm to about 2.5 mm and preferably about 0.15 mm to about 0.8 mm. Instead of one large opening at any one location, multiple small openings may be used.

Processes for manufacturing the punctal plugs useful in accordance with the present invention are well known. Typically, the punctal plugs are manufactured by injection molding, cast molding, transfer molding or the like. Preferably, the reservoir is filled with one or both of at least one active agent and the active agent-containing material subsequent to the manufacture of the plug. Additionally, one or more excipients may be combined with the active agent alone or in combination with the polymeric material.

Depending upon the active agent-containing material selected, the active agent may be released from the material almost immediately, or the active agent may be released in a sustained manner over a desired period of time. For example, a polymeric material may be used that is composed of one or more polymers that are at least partially soluble in water. When such a polymeric material is exposed to the aqueous environment of the lacrimal canaliculus or the tear fluid, it preferably will dissolve and release the active agent as it dissolves. The solubility in water of the one or more polymers from which the polymeric material is made typically will be directly proportional to its rate of dissolution. Suitable polymers that are at least partially soluble in water include poly(ethylene glycol); poly(ethylene oxide); polypropylene glycol); poly(vinyl alcohol); poly(hydroxyethyl methacrylate); poly(vinylpyrrolidone); polyacrylic acid; poly(ethyloxazoline); poly(dimethyl acrylamide); phosolipids, for example, phosphoryl choline derivatives; polysulfobetains; polysaccharides and carbohydrates, including hyaluronic acid, dextran, hydroxyethyl cellulose, hydroxyl propyl cellulose, gellan gum, guar gum, heparan sulfate, chondritin sulfate, heparin, and alginate; proteins, for example, gelatin, collagen, albumin, and ovalbumin; and polyamino acids. The polymeric materials in this list may typically be copolymerized or blended with one or both of hydrophobic polymers and monomers.

As an alternate, a non-polymeric material including a lipid, wax, or inorganic material may be used. Suitable non-polymeric materials include lanolin, paraffin, sorbates, lecithin, vitamin A, D, and E, glycerine, sorbitol, mannitol, stearates, fatty acids, lutein, zeaxanthin, taurine, glutathione and the like.

Alternately, the active agent-containing material may be one or more biodegradable polymers that partially or wholly chemically degrade upon exposure to, for example, biologically active substances typically present in mammals. The biodegradable materials are preferably hydrolyzable under in vivo conditions. Biodegradation may occur more slowly than dissolution, and the material may thus comprise one or more biodegradable polymers if slower, more sustained release of the active agent is desired.

Suitable biodegradable polymers include polymers and oligomers of glycolide, lactide, lactones, and other hydroxy acids, and other biologically degradable polymers that yield materials that are non-toxic or present as normal metabolites in the body. Preferred poly(alpha-hydroxy acids) are poly (glycolic acid), poly(2-dioxanone); poly(DL-lactic acid) and poly(L-lactic acid). Other useful polymers include poly (amino acids), polycarbonates, poly(anhydrides), poly(orthoesters), poly(phosphazines) and poly(phosphoesters). Polylactones including poly(epsilon-caprolactone), poly (delta-caprolactone), poly(delta-valerolactone) and poly (gamma-butyrolactone are also useful, as are chitosan, alginates, collagen, and gelatin. In particular aspects of the present invention, the polymeric material comprising the active agent may comprise a mixture of one or more dissolvable and bio-degradable polymers.

In a preferred exemplary embodiment, the active agent-containing material is a polymeric material that is combined with at least one active agent to form one or more fiber or fiber-like structures, the dimensions of which may be substantially the dimensions of the reservoir or smaller than such dimensions, and one or more of the fibers or fiber-like structures are inserted into the reservoir through the opening in the punctal plug main body. The fibers or fiber-like structures may be of a size and a shape suitable for insertion into the opening and may be about 0.5 to about 5 mm in length and 0.05 to about 2 mm in diameter. If only one fiber or fiber-like structure is used, preferably, the dimensions of the fiber are such that the fiber fits securely into the reservoir and remains in the reservoir when the punctal plug is in use in a wearer's punctum. Thus, the fiber may be symmetrical or asymmetrical, depending upon the shape of the reservoir. The internal walls of the reservoir may be substantially smooth or may include features that aid in maintaining the fiber within the reservoir including surfaces with grooves, indentations, roughness or the like in the interior walls.

Alternately, the fiber containing the active agent or agents may be formed and the plug cast around the fiber. As yet another alternate, the fiber and active agent may be dosed or nano-dosed into the plug reservoir as a melt and allowed to solidify. As still another alternate, the polymer and active agent may be introduced as a solution. The solution may comprise monomers, pre-polymers and the like suitable for cross-linking via one or more of irradiation, redox, and thermal radical polymerization. As yet another alternate, the fiber may simply be soaked in the active agent before or after insertion in the plug, or it may be bound throughout the silicone or EVA plug.

Preferably the fiber or fiber-like structures are composed of a polymeric material and more preferably a polymeric material that is polycaprolactone, still more preferably poly (epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about 50 percent each of polycaprolactone and ethylene vinyl acetate is used. The polymeric material used is preferably greater than about 99 percent pure and the active agent is preferably greater than about 97 percent pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded as a fiber. The fibers are then cut to the desired length and inserted into the reservoir through one or more plug openings.

The amount of active agent used in the plugs of the present invention will depend upon the active agent or agents selected, the desired doses to be delivered via the punctal plug, the desired release rate, and the melting points of the active agent and active agent-containing material. Preferably, the amount used is a therapeutically effective amount meaning an amount effective to achieve the desired treatment, inhibitory, or prevention effect. Typically, amounts of about 0.05 to about 8,000 micrograms of active agents may be used.

In certain aspects of the present invention, the reservoir may be refilled with a material after substantially all of the active agent-containing material has dissolved or degraded and the active agent is released. For example, the new active agent-containing material may be the same as, or different from, the previous polymeric material, and may contain at least one active agent that is the same as, or different from the previous active agent. Certain punctal plugs used for particular applications may preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

When the active agent-containing material is combined with the active agent, the material may also contain one or more materials that are insoluble in water and non-biodegradable, but from which the active agent can diffuse. For example, if the material is a polymeric material, the material may be composed of one or more polymers that are insoluble in water and non-biodegradable. Suitable polymers of this type include cross-liked polymers, cross-linked poly(ethylene glycol), poly(ethylene oxide), poly(propylene glycol), poly(vinyl alcohol), poly(hydroxyethyl methacrylate), poly (vinylpyrrolidone), polyacrylic acid, poly(ethyloxazoline), and poly(dimethyl acrylamide). These polymers may be copolymerized or blended with one or both of hydrophobic polymers and monomers. Additional polymers that are insoluble in water and non-biodegradable include silicone; silicone blends; silicone co-polymers including, hydrophilic monomers of pHEMA, polyethylene glycol, polyvinylpyrrolidone, and glycerol; silicone hydrogel polymers, for example, those described in U.S. Pat. Nos. 5,962,548, 6,020, 445, 6,099,852, 6,367,929, and 6,822,016, incorporated herein in their entireties by reference; phosolipids including phosphoryl choline derivatives; polysulfobetains; polysaccharides and carbohydrates including hyaluronic acid, dextran, hydroxyethyl cellulose, hydroxyl propyl cellulose, gellan gum, guar gum, heparan sulfate, chondritin sulfate, and heparin; proteins including albumin and ovalbumin; polyamino acids; fluorinated polymers including PTFE, PVDF, and teflon; polypropylene; polyethylene; nylon; and EVA. Additional examples of suitable polymers that are either or both insoluble in water and non-biodegradable include silicones, hydrophilic coatings, polyurethanes, cyanoacrylates, and polyacrylic acid.

The punctal plugs described herein may be used to deliver various active agents for the one or more of the treatment, inhibition, and prevention of numerous diseases, allergies and disorders. Each punctal plug may be used to deliver at least one active agent and may be used to deliver different types of active agents. For example, the punctal plugs may be used to deliver alcaftadine, azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The punctal plugs may be used to deliver mast cell stabilizers, for example, cromolyn sodium, lodoxamide tromethamine, nedocromil sodium, and permirolast potassium.

After the plugs are filled with the active agent, the plug is sterilized by any convenient method including ethylene oxide, autoclaving, irradiation, and the like and combination thereof. Preferably, sterilization is carried out through gamma radiation or use of ethylene oxide.

The punctal plugs may be used to deliver mydriatics and cycloplegics including atropine sulfate, homatropine, scopolamine HBr, cyclopentolate HCl, tropicamide, and phenylephrine HCl. The punctal plugs may be used to deliver ophthalmic dyes including rose bengal, lissamine green, indocyanine green, fluorexon, and fluorescein.

The punctal plugs may be used to deliver corticosteroids including dexamethasone sodium phosphate, dexamethasone, fluorometholone, fluorometholone acetate, loteprednol etabonate, prednisolone acetate, prednisolone sodium phosphate, medrysone, rimexolone, and fluocinolone acetonide. The punctal plugs may be used to deliver non-steroidal anti-inflammatory agents including flurbiprofen sodium, suprofen, diclofenac sodium, ketorolac tromethamine, cyclosporine, rapamycin methotrexate, azathioprine, and bromocriptine.

The punctal plugs may be used to deliver anti-infective agents including tobramycin, moxifloxacin, ofloxacin, gatifloxacin, ciprofloxacin, gentamicin, sulfisoxazolone diolamine, sodium sulfacetamide, neomycin, propanidine, chlorhexadine, PHMB, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The punctal plugs may be used to deliver agents for the one or more of the treatment, inhibition, and prevention of glaucoma including epinephrines, for example dipivefrin; alpha-2 adrenergic receptors, for example, aproclonidine and brimonidine; betablockers including betaxolol, carteolol, levobunolol, metipranolol, and timolol; direct miotics, including carbachol and pilocarpine; cholinesterase inhibitors, including physostigmine and echothiophate; carbonic anhydrase inhibitors including acetazolamide, brinzolamide, dorzolamide, and methazolamide; prostoglandins and prostamides including latanoprost, bimatoprost, uravoprost, and unoprostone cidofovir.

The punctal plugs may be used to deliver antiviral agents, including fomivirsen sodium, foscarnet sodium, ganciclovir sodium, valciclovir HCl, trifluridine, acyclovir, and famciclovir. The punctal plugs may be used to deliver local anesthetics including tetracaine HCl, proparacaine HCl, proparacaine HCl and fluorescein sodium, benoxinate and fluorescein sodium, and benoxnate and fluorexon disodium. The punctal plugs may be used to deliver antifungal agents including fluconazole, flucytosine, amphotericin B, itraconazole, natamycin and ketocaonazole.

The punctal plugs may be used to deliver analgesics including acetaminophen and codeine, acetaminophen and hydrocodone, acetaminophen, ketorolac, ibuprofen, and tramadol. The punctal plugs may be used to deliver vasoconstricors including ephedrine hydrochloride, naphazoline hydrochloride, phenylephrine hydrochloride, tetrahydrozoline hydrochloride, and oxymetazoline. Finally, the punctal plugs may be used to deliver vitamins, antioxidants, and nutraceuticals including vitamins A, D, and E, lutein, taurine, glutathione, zeaxanthin, fatty acids and the like.

The active agents delivered by the punctal plugs may be formulated to contain excipients including synthetic and natural polymers, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A lacrimal insert for delivering one or more active agents, the lacrimal insert comprising:
    an elongated main body having a first end and a second end, the elongated main body including a reservoir;
    a collarette connected to the first end of the main body and having at least one opening in fluid communication with the reservoir, the collarette being concentrically positioned relative to the elongated main body; and
    a head section connected to the second end of the elongated main body, the head section including a flange portion having a lower surface with a spherical cone shape and an upper surface that is substantially bowl shaped, and a cone portion; wherein the flange portion and the cone portion are non-concentrically positioned relative to the elongated main body.

2. The lacrimal insert for delivering one or more active agents according to claim 1, wherein the elongated main body comprises a substantially cylindrical shape.

3. The lacrimal insert for delivering one or more active agents according to claim 1, wherein the reservoir is positioned within the elongated main body and extends at least partially therethrough.

4. The lacrimal insert for delivering one or more active agents according to claim 3 wherein the reservoir comprises one or more active agents for the treatment of one or more of the eye, nose or throat.

5. The lacrimal insert for delivering one or more active agents according to claim 4, wherein the at least one opening in the collarette is configured to release the one or more active agents.

6. The lacrimal insert for delivering one or more active agents according to claim 1, wherein the collarette comprises a substantially disc shaped structure having a substantially flat upper and lower surface.

7. The lacrimal insert for delivering one or more active agents according to claim 6, wherein the collarette comprise a positioning mark on the upper surface.

8. The lacrimal insert for delivering one or more active agents according to claim 1, wherein the cone portion of the head section comprises at least one opening in fluid communication with the reservoir.

* * * * *